US006320002B1

(12) United States Patent
Murray et al.

(10) Patent No.: US 6,320,002 B1
(45) Date of Patent: *Nov. 20, 2001

(54) OLEFIN POLYMERIZATION CATALYST

(75) Inventors: Rex E. Murray, Cross Lanes; Simon Mawson; Clark C. Williams, both of Charleston; James D. Schreck, West Virginia, all of WV (US)

(73) Assignee: Univation Technologies, LLC, Houston, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/213,627

(22) Filed: Dec. 18, 1998

Related U.S. Application Data

(60) Provisional application No. 60/051,581, filed on Jul. 2, 1997.

(51) Int. Cl.⁷ .................................. C08F 4/80; C08F 2/34
(52) U.S. Cl. ........................... 526/89; 526/161; 526/172; 526/348.5; 526/348.6; 526/352; 526/901; 502/153; 502/167
(58) Field of Search ..................................... 526/160, 161, 526/348.6, 352, 348.5, 172, 901, 89

(56) References Cited

U.S. PATENT DOCUMENTS

| | | | |
|---|---|---|---|
| 4,001,195 | 1/1977 | Wyatt .................. | 526/348 |
| 4,508,842 | 4/1985 | Beran et al. .......... | 502/112 |
| 4,752,597 | 6/1988 | Turner ................. | 502/104 |
| 4,791,180 | 12/1988 | Turner ................. | 526/160 |
| 4,808,561 | 2/1989 | Welborn, Jr. ......... | 502/104 |
| 4,845,067 | 7/1989 | Kao et al. ............. | 502/119 |
| 4,897,455 | 1/1990 | Welborn, Jr. ......... | 526/129 |
| 4,914,253 | 4/1990 | Chang ................. | 585/523 |
| 4,923,833 | 5/1990 | Kioka et al. .......... | 502/9 |
| 4,999,327 | 3/1991 | Kao et al. ............. | 502/119 |
| 5,008,228 | 4/1991 | Chang ................. | 502/111 |
| 5,026,797 | 6/1991 | Takahashi ............ | 526/124 |
| 5,077,255 | 12/1991 | Welborn, Jr. ......... | 502/104 |
| 5,086,024 | 2/1992 | Crapo et al. .......... | 502/117 |
| 5,086,025 | 2/1992 | Chang ................. | 502/117 |
| 5,106,804 | 4/1992 | Bailly et al. .......... | 502/108 |
| 5,122,491 | 6/1992 | Kioka et al. .......... | 502/117 |
| 5,147,949 | 9/1992 | Chang ................. | 526/129 |
| 5,155,079 | 10/1992 | Cribbs et al. ......... | 502/113 |
| 5,206,199 | 4/1993 | Kioka et al. .......... | 502/117 |
| 5,240,894 | 8/1993 | Burkhardt et al. .... | 502/108 |
| 5,270,407 | 12/1993 | Takeuchi et al. ...... | 526/74 |
| 5,308,815 | 5/1994 | Sangokoya ........... | 502/104 |
| 5,318,935 | 6/1994 | Canich et al. ........ | 502/117 |
| 5,340,786 | 8/1994 | Tsutsui et al. ........ | 502/117 |
| 5,405,922 | 4/1995 | DeChellis et al. .... | 526/68 |
| 5,420,220 | 5/1995 | Cheruvu et al. ...... | 526/348 |
| 5,422,325 | 6/1995 | Jejelowo et al. ...... | 502/104 |
| 5,434,116 | 7/1995 | Sone et al. ........... | 502/103 |
| 5,466,649 | 11/1995 | Jejelowo ............. | 502/120 |
| 5,473,028 | 12/1995 | Nowlin et al. ....... | 526/114 |
| 5,516,737 | 5/1996 | Jejelowo ............. | 502/104 |
| 5,516,861 | 5/1996 | Jejelowo ............. | 526/126 |
| 5,554,704 | 9/1996 | Burkhardt et al. .... | 526/153 |
| 5,578,537 | 11/1996 | Herrmann et al. .... | 502/120 |
| 5,587,501 | 12/1996 | Winter et al. ........ | 556/53 |
| 5,595,950 | 1/1997 | Sagar et al. .......... | 502/104 |
| 5,599,885 | 2/1997 | Kawasaki et al. ..... | 526/68 |
| 5,602,217 | 2/1997 | Jejelowo ............. | 526/129 |
| 5,637,660 | 6/1997 | Nagy et al. .......... | 526/160 |
| 5,684,098 | 11/1997 | Wang et al. ......... | 526/133 |
| 5,714,427 | 2/1998 | Winter et al. ........ | 502/117 |
| 5,723,705 | 3/1998 | Herrmann et al. .... | 585/9 |
| 5,726,115 | 3/1998 | Horton et al. ........ | 502/152 |
| 5,753,578 | 5/1998 | Santi et al. .......... | 502/114 |
| 5,814,574 | 9/1998 | McNally .............. | 502/103 |
| 6,117,959 | * 9/2000 | Ponasik, Jr. et al. .. | 526/172 |

FOREIGN PATENT DOCUMENTS

| | | |
|---|---|---|
| 0803520 B1 | 12/1998 | (EP) . |
| 1015054 | 12/1965 | (GB) . |
| 1126111 | 5/1989 | (JP) . |
| WO 96/23101 | 8/1996 | (WO) . |
| WO 96/33202 | 10/1996 | (WO) . |
| WO 97/02298 | 1/1997 | (WO) . |
| WO 99/01460 | 1/1999 | (WO) . |

OTHER PUBLICATIONS

J. Organometallic Chem., Gibson et al., 550 (1998) 453–456.
J. Organometallic Chem., Orrell et al., 555 (1998) 35–47.
Inorg. Chem., Fuhrman et al., 1996, 35, 6742–6745.
Kempe et al, Octahedral Group 4 Metal Complexes . . . , Inorg. Chem. 1996, 35 6724–6745.*

* cited by examiner

Primary Examiner—David W. Wu
Assistant Examiner—R. Harlan
(74) Attorney, Agent, or Firm—Jaimes Sher; Lisa Kimes Jones; Catherine L. Bell

(57) ABSTRACT

This invention relates to a process to polymerize olefins comprising contacting an olefin with a composition comprising the product of the combination of an activator and a transition metal compound provided that if the process occurs in the slurry phase then the activator and the transition metal compound are allowed to react for at least fifteen minutes before being contacted with the olefin.

28 Claims, 2 Drawing Sheets

OLEFIN POLYMERIZATION CATALYST

STATEMENT OF RELATED APPLICATIONS

This application relates to U.S. Ser. No. 09/103,620 filed Jun. 23, 1998 now U.S. Pat. No. 6,103,657 claiming the benefit of provisional application No. 60/051,581, filed Jul. 2, 1997 and to concurrently filed U.S. patent applications, Ser. Nos., 09/215,706, and 09/216,163, and 09/216,215, all filed Dec. 18, 1998.

FIELD OF THE INVENTION

This invention relates to a process to produce bimodal polyolefin using an olefin polymerization catalysts based upon a transition metal compound comprising bidentate ligands containing pyridine or quinoline moieties.

BACKGROUND OF THE INVENTION

The intense commercialization of metallocene polyolefin catalysts has led to widespread interest in the design of non-metallocene, homogeneous catalysts. This field is more than an academic curiosity as new, non-metallocene catalysts may provide an easier pathway to currently available products and may also provide product and process opportunities which are beyond the capability of metallocene catalysts. In addition, certain non-cyclopentadienyl ligands may be more economical due to the relative ease of synthesis of a variety of substituted analogs.

Thus there is a need in the art for new novel olefin polymerization catalysts. U.S. Ser. No. 09/103,620 now U.S. Pat. No. 6,103,657 discloses the use of transition metal compounds comprising bidentate ligands containing pyridine or quinoline moieties and mixtures thereof with activators to polymerize olefins. We have found that the systems in U.S. Ser. No. 09/103,620 now U.S. Pat. No. 6,103,657 can be modified by the direct addition of an additive to produce bimodal products from a single catalyst.

SUMMARY OF THE INVENTION

This invention relates to process for polymerizing olefins comprising contacting an olefin with an olefin polymerization catalyst system comprising the product of the combination of an activator and a transition metal compound based on bidentate ligands containing pyridine or quinoline moieties, such as those described in U.S. application Ser. No. 09/103,620 filed Jun. 23, 1998, now U.S. Pat. No. 6,103,657 which is herein incorporated by reference.

DETAILED DESCRIPTION OF THE INVENTION

Figure 1:
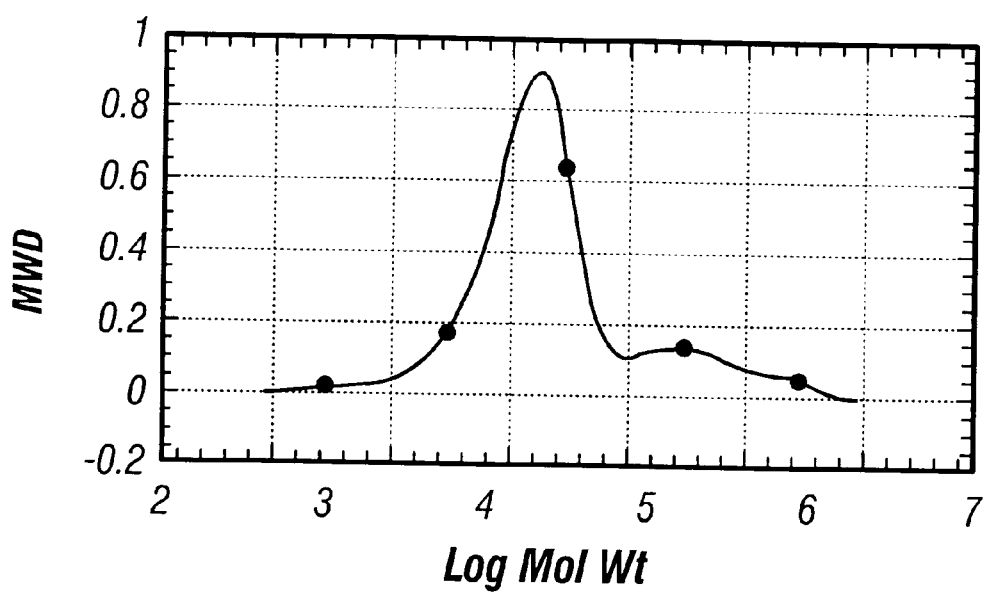
FIG. 1 is the SEC graph of Example 4.
Figure 2:
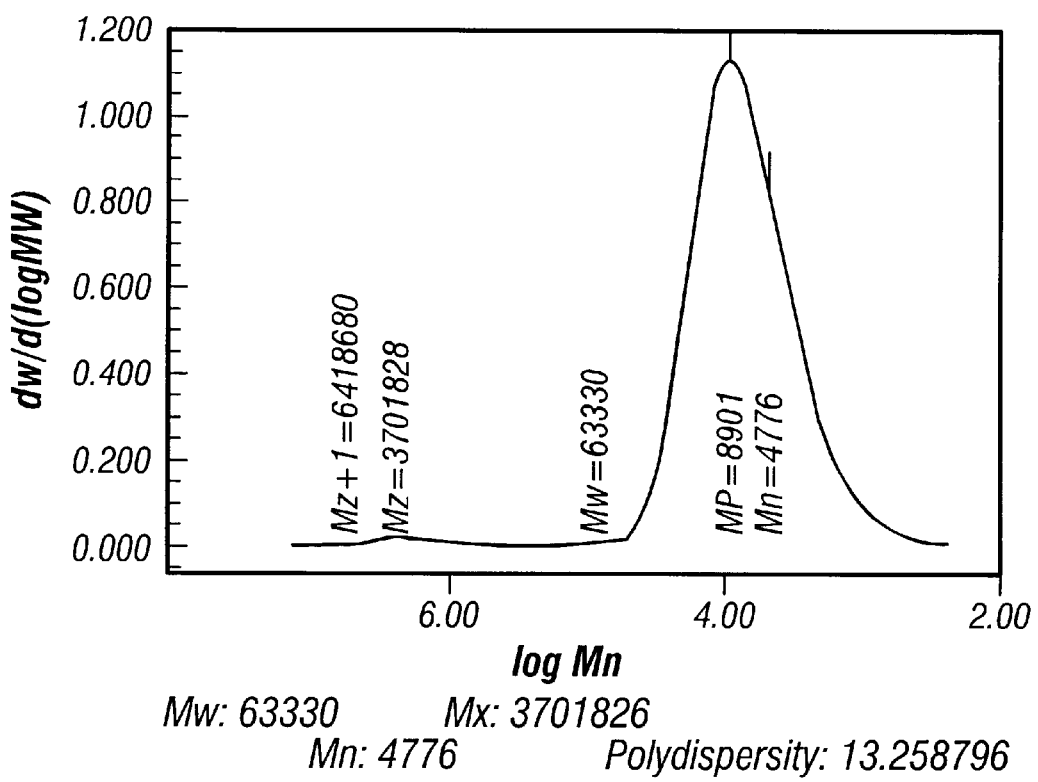
FIG. 2 is the SEC graph from Example 14 of Ser. No. 09/103,620 filed Jun. 23, 1998 now U.S. Pat. No. 6,103,657.

This invention relates to a process to produce polyolefins using an olefin polymerization catalyst system comprising the product of the combination of an activator and a transition metal compound based on bidentate ligands containing pyridine or quinoline moieties.

The activator may be any known catalyst activator and in one embodiment is an alkyl aluminum, an alumoxane, a modified alumoxane, polyalumoxane, a non-coordinating anion, a Lewis acid or a mixture thereof.

There are a variety of methods for preparing alumoxane and modified alumoxanes, non-limiting examples of which are described in U.S. Pat. Nos. 4,665,208, 4,952,540, 5,091, 352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253 and 5,731,451 and European publications EP-A-0 561 476, EP-B1-0 279 586 and EP-A-0 594-218, and PCT publication WO 94/10180, all of which are herein fully incorporated by reference.

Ionizing compounds (non-coordinating anions) may contain an active proton, or some other cation associated with but not coordinated to or only loosely coordinated to the remaining ion of the ionizing compound. Such compounds and the like are described in European publications EP-A-0 570 982, EP-A-0 520 732, EP-A-0 495 375, EP-A-0 426 637, EP-A-500 944, EP-A-0 277 003 and EP-A-0 277 004, and U.S. Pat. Nos. 5,153,157, 5,198,401, 5,066,741, 5,206, 197, 5,241,025, 5,387,568, 5,384,299 and 5,502,124 and U.S. patent application Ser. No. 08/285,380, filed Aug. 3, 1994, now abandoned all of which are herein fully incorporated by reference. Other activators include those described in PCT publication WO 98/07515 such as tris(2, 2',2"-nonafluorobiphenyl)fluoroaluminate, which is fully incorporated herein by reference. Combinations of activators are also contemplated by the invention, for example, alumoxanes and ionizing activators in combinations, see for example, PCT publications WO 94/07928 and WO 95/14044 and U.S. Pat. Nos. 5,153,157 and 5,453,410 all of which are herein fully incorporated by reference. Also, methods of activation such as using radiation and the like are also contemplated as activators for the purposes of this invention.

In a preferred embodiment, activator is selected from the following: tris(2,2',2"-nonafluorobiphenyl)fluoroaluminate, alumoxane, tris(2,2',2"-nonafluorobiphenyl) fluoroaluminate, triphenyl boron, triethyl boron, tri-n-butyl ammonium tetraethylborate, triaryl borane, tri(n-butyl) ammonium tetrakis(pentafluorophenyl)boron or a trisperfluorophenyl boron, or diethylaluminum chloride.

The transition metal compound is preferably represented by the formula:

$$((Z)XA_t(YJ))_q MQ_n T_s \quad\quad (I)$$

where M is a metal selected from Group 3 to 13 or lanthanide and actinide series of the Periodic Table of Elements; T is bonded to M and is an element from Group 13 to 16, preferably oxygen, boron, nitrogen, silicon, phosphorus, sulfur or aluminum and T may also be bound to one or more C1 to C50 groups optionally containing one or more heteroatoms, preferably T is a hydrocarboxy group, a boronate group or an amide group, preferably an alkoxide, phenoxide, acetylacetonate, or carboxylate or a cyclopentadienide group such as cyclopentadienyls, flourenyls and indenyls, Q is bonded to M and each Q is a monovalent, divalent or trivalent anion; X and Y are bonded to M; X and Y are independently C or a heteroatom, provided that at least one of X and Y is a heteroatom, preferably both X and Y are heteroatoms; Y is contained in a heterocyclic ring J, where J comprises from 2 to 50 non-hydrogen atoms, preferably 2 to 30 carbon atoms; Z is bonded to X, where Z comprises 1 to 50 non-hydrogen atoms, preferably 1 to 50 carbon atoms, preferably Z is a cyclic group containing 3 to 50 atoms, preferably 3 to 30 carbon atoms, alternately Z may be a silyl group, preferably an alkyl silyl group; t is 0 or 1; when t is 1, A is a bridging group joined to at least one of X, Y or J, preferably X and J; q is 1 or 2; m is the oxidation state of M minus q minus s if Q is a monovalent anion, n is (the oxidation state of M−q−s)/2, if Q is a bivalent anion or n is (the oxidation state of M−q−s)/3 if Q is a trivalent anion, preferably n is an integer from 1 to 3, s is 1, 2 or 3, preferably 1 or 2. In one embodiment, where X is oxygen or sulfur then Z is optional. In another embodiment, where X is nitrogen or phosphorous then Z is present. In a preferred embodiment T is oxygen and is bound to an alkyl, aryl, or alkaryl group.

In another embodiment, at least one of the transition metal catalyst compounds is represented by the formula:

$$((R'_mZ)XA(YJR''_p))_qMQ_nT_s \qquad (II)$$

where M is a metal selected from Group 3 to 13 of the Periodic Table of Elements, preferably a Group 4 to 12 transition metal, more preferably a Group 4, 5 or 6 transition metal, even more preferably a Group 4 transition metal such as titanium, zirconium or hafnium, and most preferably zirconium;

T is bonded to M and is an element from Group 13 to 16, preferably oxygen, boron, nitrogen, silicon, phosphorus, sulfur or aluminum and T may also be bound to one or more C1 to C50 groups optionally containing one or more heteroatoms, T is preferably a hydrocarboxy group, a boronate, or an amide, preferably an alkoxide, phenoxide, acetylacetonate, or carboxylate or a cyclopentadienide group such as cyclopentadienyls, flourenyls and indenyls.

Each Q is bonded to M and each Q is a monovalent, divalent or trivalent anion. Preferably each Q is independently selected from the group consisting of halogens, hydrogen, alkyl, aryl, alkenyl, alkylaryl, arylalkyl, hydrocarboxy or phenoxy radicals having 1–20 carbon atoms. Each Q may also be amides, phosphides, sulfides, silylalkyls, diketonates, and carboxylates. Optionally, each Q may contain one or more heteroatoms, more preferably each Q is selected from the group consisting of halides, alkyl radicals and arylalkyl radicals. Most preferably, each Q is selected from the group consisting of arylalkyl radicals such as benzyl.

X and Y are independently C or a heteroatom, provided that at least one of X and Y is a heteroatom, X and Y are preferably each heteroatoms, more preferably independently selected from the group consisting of nitrogen, oxygen, sulfur and phosphorous, even more preferably nitrogen or phosphorous, and most preferably nitrogen;

Y is contained in a heterocyclic ring or ring system J. J contains from 2 to 30 carbon atoms, preferably from 2 to 7 carbon atoms, more preferably from 3 to 6 carbon atoms, and most preferably 5 carbon atoms. Optionally, the heterocyclic ring J containing Y, may contain additional heteroatoms. J may be substituted with R'' groups that are independently selected from the group consisting of hydrogen or linear, branched, cyclic, alkyl radicals, or alkenyl, alkynyl, alkoxy, aryl or aryloxy radicals. Also, two or more R'' groups may be joined to form a cyclic moiety such as an aliphatic or aromatic ring. Preferably R'' is hydrogen or an aryl group, most preferably R'' is hydrogen. When R'' is an aryl group and Y is nitrogen, a quinoline group is formed. Optionally, an R'' may be joined to A;

Z is a hydrocarbyl group bonded to X, preferably Z is a hydrocarbyl group of from 1 to 50 carbon atoms, preferably Z is a cyclic group having from 3 to 30 carbon atoms, preferably Z is a substituted or unsubstituted cyclic group containing from 3 to 30 carbon atoms, optionally including one or more heteroatoms, Z may be a silyl group, an alkylsilyl group or a trialkyl, in another embodiment Z is not an aryl group;

Z may be substituted with R' groups that are independently selected from group consisting of hydrogen or linear, branched, alkyl radicals or cyclic alkyl, alkenyl, or alkynyl radicals. Also, two or more R' groups may be joined to form a cyclic moiety such as an aliphatic or aromatic ring. Preferably R' is an alkyl group having from 1 to 20 carbon atoms, more preferably R' is methyl, ethyl, propyl, butyl, pentyl and the like, including isomers thereof, more preferably R' is a methyl group or a primary, secondary or tertiary hydrocarbon, including isopropyl, t-butyl and the like, most preferably R' is an isopropyl group. Optionally, an R' group may be joined to A. It is preferred that at least one R' is ortho to X;

A is a bridging group joined to at least one of, preferably both of, X and J. Bridging group A contains one or more Group 13 to 16 elements from Periodic Table of Elements. More preferably A contains one or more Group 14 elements, most preferably A is a substituted carbon group, a di-substituted carbon group or vinyl group; and In formula (II) m and p are independently an integer from 0 to 5, preferably m is 2; s is an integer from 1 to 3; and q is 1 or 2, n is the oxidation state of M minus q minus s if Q is a monovalent anion, n is (the oxidation state of M−q−s)/2, if Q is a bivalent anion or n is (the oxidation state of M−q−s)/3 if Q is a trivalent anion, and where q is 2, the two ((R'_mZ)XA(YJR''_p)) of formula (IV) are bridged to each other via a bridging group, preferably a bridging group containing a Group 14 element.

In one embodiment J is pyridine in either of the above formulae.

In a preferred embodiment the transition metal compound is [[1-(2-Pyridyl)N-1-Methylethyl]-[1-N-2,6-Diisopropylphenyl Amido]][2-Methyl-1-Phenyl-2-Propoxy] Zirconium Dibenzyl.

In another preferred embodiment [[1-(2-Pyridyl)N-1-Methylethyl]-[1-N-2,6-Diisopropylphenyl Amido]][2-Methyl-1-Phenyl-2-Propoxy]Zirconium Dibenzyl is used in combination with an alumoxane, preferably a methyl alumoxane, more preferably a modified methyl alumoxane in a gas phase or slurry reactor to produce polyethylene, preferably high density polyethylene. In another preferred embodiment a non-coordinating anion, such as tri(n-butyl) ammonium tetrakis(pentafluorophenyl)boron or a trisperfluorophenyl boron, is used in combination with the [[1-(2-Pyridyl)N-1-Methylethyl]-[1-N-2,6-Diisopropylphenyl Amido]][2-Methyl-1-Phenyl-2-Propoxy]Zirconium Dibenzyl in a gas phase or slurry phase reactor. In another embodiment the actovator is selected form the following: tris(2,2',2"-nonafluorobiphenyl)fluoroaluminate, alumoxane, tris(2,2',2"-nonafluorobiphenyl) fluoroaluminate, triphenyl boron, triethyl boron, tri-n-butyl ammonium tetraethylborate, triaryl borane, tri(n-butyl) ammonium tetrakis(pentafluorophenyl)boron or a trisperfluorophenyl boron, or diethylaluminum chloride.

The transition metal compounds may be made by any method known in the art.

The catalyst systems or components thereof may be supported on an organic or inorganic support. Typically the support can be of any of the solid, porous supports. Typical support materials include talc; inorganic oxides such as silica, magnesium chloride, alumina, silica-alumina; polymeric supports such as polyethylene, polypropylene, polystyrene; and the like. Preferred supports include silica, clay, talc magnesium chloride and the like. Preferably the support is used in finely divided form. Prior to use the support is preferably partially or completely dehydrated. The dehydration may be done physically by calcining or by chemically converting all or part of the active hydroxyls. For more information on how to support catalysts please see U.S. Pat. No. 4,808,561 which teaches how to support a metallocene catalyst system. The techniques used therein are generally applicable for this invention.

The transition metal compound and activator may be placed on the same support or may be placed on separate support. The catalysts/catalyst systems and/or their components need not be feed into the reactor in the same manner. For example, the transition metal compound or its components may be slurried into the reactor on a support while the activator is provided in a solution.

In a preferred embodiment the catalyst system is fed into the reactor in a solution or slurry. Hydrocarbons are useful for the solutions or slurries. For example the solution can be toluene, hexane, isopentane or a combination thereof such as toluene and isopentane or toluene and pentane. A typical solution would be 0.02 to 0.05 mole catalyst in the hydrocarbon carrier, preferably isopentane or hexane.

In another preferred embodiment the one or all of the catalysts are combined with up to 6 weight % of a metal stearate, (preferably a aluminum stearate, more preferably aluminum distearate) based upon the weight of the catalyst, any support and the stearate, preferably 2 to 3 weight %. In an alternate embodiment a solution of the metal stearate is fed into the reactor. These agents may be dry tumbled with the catalyst or may be fed into the reactor in a solution with or without the catalyst system or its components. In a preferred embodiment the catalysts combined with the activators are tumbled with 1 weight % of aluminum distearate and/or 2 weight % of an antistat, such as a methoxylated amine, such as Witco's Kemamine AS-990 from ICI Specialties in Bloomington Del. The metal stearate and/or the anti-static agent may be slurried into the reactor in mineral oil, ground into a powder then suspended in mineral oil then fed into the reactor, or blown directly into the reactor as a powder.

More information on using aluminum stearate type additives may be found in U.S. Ser. No. 09/113,216 filed Jul. 10, 1998, which is incorporated by reference herein.

In another embodiment the transition metal catalyst compound and activator are fed into the reactor separately from the additive.

In a preferred embodiment of the invention, it has been observed that temperature apparently affects the catalyst and apparently produces another species. While not wishing to bound by any theory it appears that this conversion provides the ability to produce bimodal product. Thus we have noted that higher temperatures produce more bimodal product.

Polymerization Process of the Invention

The catalysts and catalyst systems described above are suitable for use as a solution, gas or slurry polymerization process or a combination thereof, most preferably a gas or slurry phase polymerization process.

In one embodiment, this invention is directed toward the solution, slurry or gas phase polymerization reactions involving the polymerization of one or more of monomers having from 2 to 30 carbon atoms, preferably 2–12 carbon atoms, and more preferably 2 to 8 carbon atoms. Preferred monomers include one or more of ethylene, propylene, butene-1, pentene-1,4-methyl-pentene-1, hexene-1, octene-1, decene-1,3-methyl-pentene-1, and cyclic olefins or a combination thereof. Other monomers can include vinyl monomers, diolefins such as dienes, polyenes, norbornene, norbornadiene monomers. Preferably a homopolymer of ethylene is produced. In another embodiment, a copolymer of ethylene and one or more of the monomers listed above is produced.

In another embodiment ethylene or propylene is polymerized with at least two different comonomers to form a terpolymer. The preferred comonomers are a combination of alpha-olefin monomers having 4 to 10 carbon atoms, more preferably 4 to 8 carbon atoms, optionally with at least one diene monomer. The preferred terpolymers include the combinations such as ethylene/butene-1/hexene-1, ethylene/propylene/butene-1, propylene/ethylene/hexene-1, ethylene/propylene/norbornene and the like.

In a particularly preferred embodiment the process of the invention relates to the polymerization of ethylene and at least one comonomer having from 4 to 8 carbon atoms, preferably 4 to 7 carbon atoms. Particularly, the comonomers are butene-1,4-methyl-pentene-1,3-methyl-pentene-1, hexene-1 and octene-1, the most preferred being hexene-1, butene-1 or octene-1.

Typically in a gas phase polymerization process a continuous cycle is employed where in one part of the cycle of a reactor system, a cycling gas stream, otherwise known as a recycle stream or fluidizing medium, is heated in the reactor by the heat of polymerization. This heat is removed from the recycle composition in another part of the cycle by a cooling system external to the reactor. Generally, in a gas fluidized bed process for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661 and 5,668,228 all of which are fully incorporated herein by reference.)

The reactor pressure in a gas phase process may vary from about 10 psig (69 kPa) to about 500 psig (3448 kPa), preferably in the range of from about 200 psig (1379 kPa) to about 400 psig (2759 kPa), more preferably in the range of from about 250 psig (1724 kPa) to about 350 psig (2414 kPa).

The reactor temperature in the gas phase process may vary from about 30° C. to about 120° C., preferably from about 60° C. to about 115° C., more preferably in the range of from about 70° C. to about 110° C., and most preferably in the range of from about 70° C. to about 95° C.

The productivity of the catalyst or catalyst system in a gas phase system is influenced by the main monomer partial pressure. The preferred mole percent of the main monomer, ethylene or propylene, preferably ethylene, is from about 25 to 90 mole percent and the monomer partial pressure is in the range of from about 75 psia (517 kPa) to about 300 psia (2069 kPa), which are typical conditions in a gas phase polymerization process.

In a preferred embodiment, the reactor utilized in the present invention is capable and the process of the invention is producing greater than 500 lbs of polymer per hour (227 Kg/hr) to about 200,000 lbs/hr (90,900 Kg/hr) or higher of polymer, preferably greater than 1000 lbs/hr (455 Kg/hr), more preferably greater than 10,000 lbs/hr (4540 Kg/hr), even more preferably greater than 25,000 lbs/hr (11,300 Kg/hr), still more preferably greater than 35,000 lbs/hr (15,900 Kg/hr), still even more preferably greater than 50,000 lbs/hr (22,700 Kg/hr) and most preferably greater than 65,000 lbs/hr (29,000 Kg/hr) to greater than 100,000 lbs/hr (45,500 Kg/hr).

Other gas phase processes contemplated by the process of the invention include those described in U.S. Pat. Nos.

5,627,242, 5,665,818 and 5,677,375, and European publications EP-A-0 794 200, EP-A-0 802 202 and EP-B-634 421 all of which are herein fully incorporated by reference.

A slurry polymerization process generally uses pressures in the range of from about 1 to about 50 atmospheres and even greater and temperatures in the range of 0° C. to about 120° C. In a slurry polymerization, a suspension of solid, particulate polymer is formed in a liquid polymerization diluent medium to which ethylene and comonomers along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process must be operated above the reaction diluent critical temperature and pressure. Preferably, a hexane or an isobutane medium is employed.

In one embodiment, a preferred polymerization technique of the invention is referred to as a particle form polymerization, or a slurry process where the temperature is kept below the temperature at which the polymer goes into solution. Such technique is well known in the art, and described in for instance U.S. Pat. No. 3,248,179 which is fully incorporated herein by reference. The preferred temperature in the particle form process is within the range of about 185° F. (85° C.) to about 230° F. (110° C.). Two preferred polymerization methods for the slurry process are those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484, which is herein fully incorporated by reference.

In another embodiment, the slurry process is carried out continuously in a loop reactor. The catalyst as a slurry in isobutane or as a dry free flowing powder is injected regularly to the reactor loop, which is itself filled with circulating slurry of growing polymer particles in a diluent of isobutane containing monomer and comonomer. Hydrogen, optionally, may be added as a molecular weight control. The reactor is maintained at pressure of about 525 psig to 625 psig (3620 kPa to 4309 kPa) and at a temperature in the range of about 140° F. to about 220° F. (about 60° C. to about 104° C.) depending on the desired polymer density. Reaction heat is removed through the loop wall since much of the reactor is in the form of a double-jacketed pipe. The slurry is allowed to exit the reactor at regular intervals or continuously to a heated low pressure flash vessel, rotary dryer and a nitrogen purge column in sequence for removal of the isobutane diluent and all unreacted monomer and comonomers. The resulting hydrocarbon free powder is then compounded for use in various applications.

In another embodiment, the reactor used in the slurry process of the invention is capable of and the process of the invention is producing greater than 2000 lbs of polymer per hour (907 Kg/hr), more preferably greater than 5000 lbs/hr (2268 Kg/hr), and most preferably greater than 10,000 lbs/hr (4540 Kg/hr). In another embodiment the slurry reactor used in the process of the invention is producing greater than 15,000 lbs of polymer per hour (6804 Kg/hr), preferably greater than 25,000 lbs/hr (11,340 Kg/hr) to about 100,000 lbs/hr (45,500 Kg/hr).

In another embodiment in the slurry process of the invention the total reactor pressure is in the range of from 400 psig (2758 kPa) to 800 psig (5516 kPa), preferably 450 psig (3103 kPa) to about 700 psig (4827 kPa), more preferably 500 psig (3448 kPa) to about 650 psig (4482 kPa), most preferably from about 525 psig (3620 kPa) to 625 psig (4309 kPa).

In yet another embodiment in the slurry process of the invention the concentration of ethylene in the reactor liquid medium is in the range of from about 1 to 10 weight percent, preferably from about 2 to about 7 weight percent, more preferably from about 2.5 to about 6 weight percent, most preferably from about 3 to about 6 weight percent. A preferred process of the invention is where the process, preferably a slurry or gas phase process is operated in the absence of or essentially free of any scavengers, such as triethylaluminum, trimethylaluminum, tri-isobutylaluminum and tri-n-hexylaluminum and diethyl aluminum chloride, dibutyl zinc and the like. This preferred process is described in PCT publication WO 96/08520 and U.S. Pat. No. 5,712,352, which are herein fully incorporated by reference.

In another embodiment the process is run with scavengers. Typical scavengers include trimethyl aluminum, tri-isobutyl aluminum and an excess of alumoxane or modified alumoxane.

The proportions of the components of the feed catalyst solution can be varied to alter molecular weight and other properties. Another method to alter the molecular weight is to add hydrogen to the system by increasing the hydrogen ethylene ratio. A method to control the density is altering the comonomer content.

A method to control molecular weight distribution (Mw/Mn), flow index, and/or density comprising altering on line in a commercial scale gas phase reactor (i.e. having a volume of 1500 cubic feet or more) the reaction temp and/or the hydrogen concentration and/or the activator to transition metal ratio, such as the aluminum/zirconium ratio is also provided herein.

Injection and mixing temperatures also provide a means to alter product properties as temperature affects activation and/or solvent evaporation and thus alters the catalyst composition and hence alters the final product.

The sequence and timing of activation also provides an opportunity to alter the catalyst composition and thus the final product. For example higher concentrations of methyl alumoxane in a system comprising [[1-(2-Pyridyl)N-1-Methylethyl]-[1-N-2,6-Diisopropylphenyl Amido]][2-Methyl-1-Phenyl-2-Propoxy]Zirconium Dibenzyl will alter the balance of products formed by the catalyst. This includes higher concentrations during activation and/or mixing and/or transport and/or in spraying into the reactor. Likewise we have noted that increasing the hydrocarbon carrier in the catalyst feed increased the amount of lower molecular weight fraction produced.

One can also vary the product by altering the reaction temperature. We have noted that raising the reaction temperature increased the amount of the higher molecular weight component and unusually the two modes in the size exclusion chromatography graph moved closer together (that is the Mw/Mn became lower when compared to the same system at a lower temperature).

One can also vary the molecular weight distribution by varying the reactor temperature, varying the temperature of the catalyst system before it enters the reactor, varying the catalyst to activator ratio, varying the volume of the carrier, and/or contacting the transition metal component with solvent prior to activation with the activator.

In another preferred embodiment the catalyst system in is liquid form and is introduced into the reactor into a resin particle lean zone. For information on how to introduce a liquid catalyst system into a fluidized bed polymerization into a particle lean zone, please see U.S. Pat. No. 5,693,727, which is incorporated by reference herein.

In another preferred embodiment, the transition metal compound is contacted with solvent prior to contact with the activator.

In a preferred embodiment, the polyolefin recovered typically has a melt index as measured by ASTM D-1238, Condition E, at 190° C. of 1 g/10 min or less. In a preferred embodiment the polyolefin is ethylene homopolymer or copolymer. The comonomer is preferably a C3 to C20 linear branched or cyclic monomer, and in one embodiment is a C3 to C12 linear or branched alpha-olefin, preferably propylene, hexene, pentene, hexene, heptene, octene, nonene, decene, dodecene, 4-methyl-pentene-1,3-methyl pentene-1,3,5,5-trimethyl hexene 1, and the like.

In a preferred embodiment the catalyst system described above is used to make a high density polyethylene having a density of between 0.925 and 0.965 g/cm³ (as measured by ASTM 2839), a melt index of 1.0 or less g/10 min or less (as measured by ASTM D-1238, Condition E, at 190° C.).

The polyolefins then can be made into films, molded articles, sheets and the like. The films may be formed by any of the conventional technique known in the art including extrusion, co-extrusion, lamination, blowing and casting. The film may be obtained by the flat film or tubular process which may be followed by orientation in an uniaxial direction or in two mutually perpendicular directions in the plane of the film to the same or different extents. Particularly preferred methods to form the polymers into films include extrusion or coextrusion on a blown or cast film line.

The films produced may further contain additives such as slip, antiblock, antioxidants, pigments, fillers, antifog, UV stabilizers, antistats, polymer processing aids, neutralizers, lubricants, surfactants, pigments, dyes and nucleating agents. Preferred additives include silicon dioxide, synthetic silica, titanium dioxide, polydimethylsiloxane, calcium carbonate, metal stearates, calcium stearate, zinc stearate, talc, $BaSO_4$, diatomaceous earth, wax, carbon black, flame retarding additives, low molecular weight resins, glass beads and the like. The additives may be present in the typically effective amounts well known in the art, such as 0.001 weight % to 10 weight %.

EXAMPLES

MFR Melt Flow Ratio was measured by ASTM 1238.

BBF (butyl branch frequency per 1000 carbon atoms) was measured by infrared spectroscopy as describe in U.S. Pat. No. 5,527,752.

PDI (polydispersity index) is Mw/Mn and was measured by Size Exclusion Chromotography.

Melt Index (MI) was measured by the procedure according to ASTM 123 8, condition E.

Melt Index Ratio (MIR) is the ratio of $I_{21}$ over $I_2$ as measured by the procedure according to ASTM D 1238.

Density is measured according to ASTM D 1505.

MMAO 3A is modified methyl alumoxane commercially available from Akzo Chemicals, Inc. under the trade name Modified Methylalumoxane type 3A, covered under U.S. Pat. No. 5,041,584.

Example 1

Preparation Of [1-(2-Pyridyl)N-1-Methylethyl][1-N-2,6-Diisopropylphenyl]Amine

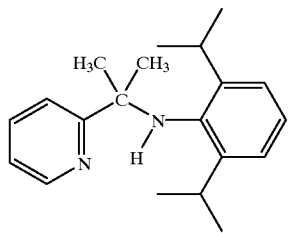

In a dry box, 22.45 mmol (6.34 g) 2-acetylpyridine(2,6-diisopropylphenylimine) were charged to a 250 mL round bottom flask equipped with a stir bar and septa. The flask was sealed, removed from the dry box and placed under nitrogen purge. Dry toluene (50 mL) was added and stirred to dissolve the ligand. The vessel was chilled to 0° C. in a wet ice bath. Trimethyl aluminum (Aldrich, 2.0 M in toluene) was added dropwise over ten minutes. The temperature of the reaction was not allowed to exceed 10° C. When addition of the trimethyl aluminum was complete, the mixture was allowed to warm slowly to room temperature, and then was then placed in an oil bath and heated to 40° C. for 25 minutes. The vessel was removed from the oil bath and placed in an ice bath. A dropping funnel containing 100 mL of 5% KOH was attached to the flask. The caustic was charged to the reaction dropwise over a 1 hour span. The mixture was transferred to a separatory funnel. The aqueous layer was removed. The solvent layer was washed with 100 mL water then 100 mL brine. The red-brown liquid product was dried over $Na_2SO_4$, vacuum stripped and placed under high vacuum over night.

80 mL of red-brown liquid was transferred to a 200 mL Schlenk flask equipped with a stir bar. A distillation head with a dry ice condenser was attached to the flask. The mixture was vacuum distilled yielding approximately 70 g of dark yellow viscous liquid product.

Example 2

Preparation Of [1-(2-Pyridyl)N-1-Methylethyl][1-N-2,6-Diisopropylphenyl Amido]Zirconium Tribenzyl

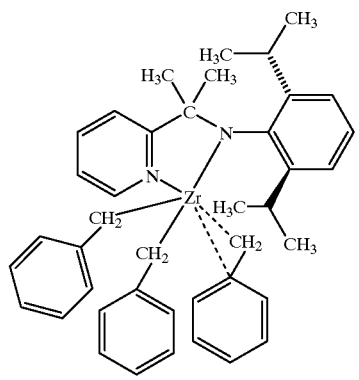

In a darkened room and darkened dry box, 5.0 mmol (1.45 g) of the ligand made in Example 1 were charged to a 100 mL Schlenk tube equipped with a stir bar. The ligand was dissolved in 5 mL of toluene. To a second vessel equipped with a stir bar was charged 5.5 mmol (2.5 g) tetrabenzyl zirconium and 10 mL toluene.

The ligand solution was transferred into the tetrabenzyl zirconium solution. The vessel was covered with foil and allowed to stir at room temperature in the dry box. After 6 hours at room temperature 80 mL dry hexane was added to the reaction solution and allowed to stir overnight. The reaction mixture was filtered through a medium porosity frit with approximately 2 g pale yellow solids collected.

Example 3

Preparation Of [[1-(2-Pyridyl)N-1-Methylethyl]-[1-N-2,6-Diisopropylphenyl Amido]][2-Methyl-1-Phenyl-2-Propoxy]Zirconium Dibenzyl

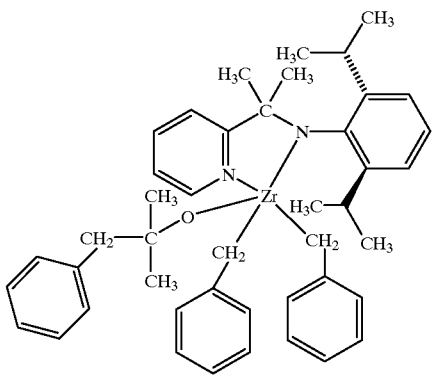

To an oven-dried, cooled, purged and sealed GC vial was charged 0.10 mL dried acetone. The GC vial was sealed in a shell vial and taken into the dry box. In a darkened room and darkened dry box 2.0 mmol (1.3 g) of the material made in Example 2 and 9 mL toluene were charged to 1 100 mL Schlenk flask equipped with a stir bar. To a second GC vial was charged 2.0 mmol (146 uL) acetone and 1.0 mL toluene. The acetone/toluene solution was transferred dropwise via syringe into the stirred solution of [1-(2pyridyl)N-1-methylethyl][1-N-2,6-diisopropylphenylamido]zirconium tribenzyl. The vessel was covered with foil and allowed to stir at room temperature in the dry box overnight.

The reaction solution was vacuum stripped to a tacky orange residue. Dry hexane (20 mL) was added and the residue stirred vigorously, then vacuum stripped again to a yellow-orange glass. Hexane was added again and vigorously stirred. The vessel was placed in a freezer (−24° C.) for approximately 2 hours. The mixture was filtered through a medium porosity frit. Pale yellow solids (0.8 g) were collected. Slow deliberate feeding of the acetone with good mixing appears best.

Example 4

A bimodal ethylene/hexene copolymer was made in a laboratory scale slurry phase reactor using the complex prepared in Example 3 according to the invention with MMAO type 3A cocatalyst. In this experiment MMAO 3A was allowed to react 4 hours in toluene with the complex prepared in example 3 prior to conducting the polymerization reaction.

In a dry box, toluene (0.4 mLs, alumina dried) was charged to an oven dried, 4 dram glass vial. And the complex prepared in Example 3 (2.0 micromoles, 0.067 mL of an 0.030M solution in deuterated benzene) was added to the toluene resulting in a pale yellow solution. MMAO type 3A (1.0 mmoles. 0.52 mL, 1.89M, 7.0 wt % in heptane solvent) was then added to the vial resulting in an 0.002026M pale yellow reaction solution. The vial was then encased in aluminum foil.

After 4.0 hours, 0.25 mLs (0.5 μmoles Zr, 0.25 mmoles MMAO) of the reaction solution was charged to the reactor containing 600 mLs n-hexane, 43 mLs 1-hexene, and 0.13 mLs (0.25 mmoles, 1.89M, 7.0 wt % in heptane solvent) MMAO type 3A. The reactor was run at 85° C. and 85 psi ethylene for 30 minutes. The reaction produced 44.3 g of polyethylene resin (activity=208471 g polyethylene/mmole Zr/hour/100 psi ethylene, 12=20.9, I21=824.1, BBF=9.5 butyl branches/1000 $CH_2$ Size Exclusion Chromatography (SEC) revealed the following molecular weight properties: Mn=9123, Mw=104852, PDI=11.49. The SEC graph is presented as FIG. 1.

Example 5

An ethylene hexene copolymer was produced in a 14 inch pilot plant gas phase reactor operating at 85° C., 220 psi (1517 kPa) having a water cooled heat exchanger. The ethylene was fed in at a rate of about 55 pounds of ethylene per hour (25 kg/hr) and hexene was fed in at 1.4 pounds per hour(0.64 kg/hr) and hydrogen was fed in at rate of 0.021 pounds per hour (0.01 kg/hr) to make about 35 pounds per hour (15.9 kg/hr) of polymer. Total reactor pressure was 350 psi (2413 kPa). The nitrogen was present at about 3–7 pounds/hour (1.4 kg–3.2 kg). The reactor was equipped with a plenum set at 1800 pounds per hour (818.2 kg/hr) with a single hole tapered nozzle injector having a 0.055 inch (0.14 cm) inside diameter. The catalyst was the compound produced in Example 3. This procedure was repeated and one or more of the reaction temperature, the Al/Zr ratio, the injection temperature or the hydrocarbon feed carrier were varied as reported in Table 2. (The plenum is a device used to create a particle lean zone in a fluidized bed gas phase reactor. For more information on plenum usage see U.S. Pat. No. 5,693,727.)

TABLE 2

| Example | Rxn temp | Wt % low Mw | Mw/Mn | Al:Zr ratio |
| --- | --- | --- | --- | --- |
| A | 85 | 60 | 14 | 350:1::Al:Zr |
| B | 90 | 57 | 16 | 360:1::AL:Zr |
| C | 95 | 51 | 12 | 350:1::Al:Zr |
| D | 105 | 35 | 11 | 350:1::Al:Zr |
| F | 85 | 70 |  | 72:1::Al:Zr |

"Wt % low Mw" is the weight % of the lower molecular weight species produced as characterized by Size Exclusion Chromatography using a log normal Gaussian deconvolution.

All documents described herein are incorporated by reference herein, including any priority documents and/or testing procedures. As is apparent form the foregoing general description and the specific embodiments, while forms of the invention have been illustrated and described, various modifications can be made without departing from the spirit and scope of the invention. Accordingly it is not intended that the invention be limited thereby.

What is claimed is:

1. A process to polymerize olefins comprising contacting an olefin with a composition comprising the product of the combination of an activator and a transition metal compound which is represented by the formulae:

$$((Z)XA_t(YJ))_q MQ_n T_s \quad (I)$$

or $$((R'_m Z)XA_t(YJR''_p))_q MQ_n \quad (II)$$

wherein M is a metal selected from a group consisting of Group 3 to 13 transition metal and lanthanide and actinide series of the Periodic Table of Elements; T is bonded to M and is an element from Group 13 to 16 and T may also be bound to one or more C1 to C50 groups; Q is bonded to M and each Q is a monovalent, bivalent or trivalent anion; X and Y are bonded to M; X and Y are independently C or a heteroatom, provided that at least one of X and Y is a heteroatom and Y is contained in a heterocyclic ring J, wherein J comprises from 2 to 50 non-hydrogen atoms; Z is bonded to X, wherein Z comprises 1 to 50 non-hydrogen atoms; t is 0 or 1; when t is 1, A is a bridging group joining X and J; q is 1 or 2; n is (the oxidation state of M -q-s)/2, if Q is a bivalent anion, or n is (the oxidation state of M q-s)/3 if Q is a trivalent anion, s is 1,2 or 3;

- R" groups are independently selected from the group consisting of hydrogen or linear, branched, cyclic, alkyl radicals, or alkenyl, alkynyl, alkoxy, aryl or aryloxy radicals and two or more R" groups may be joined to form a cyclic moiety, optionally, an R" may be joined to A;
- R' groups that are independently selected from a group consisting of hydrogen or linear, branched, alkyl radicals or cyclic alkyl, alkenyl, alkynyl or aryl radicals, two or more R' groups may be joined to form a cyclic moiety, optionally, an R' group may be joined to A;
- m p are independently an integer from 0 to 5;
- and when q is 2, the two $((R'_m Z)XA_t(YJR''_p))$ of formula (II) are bridged to each other via a bridging group,
- provided that if the process occurs in the slurry phase then the activator and the transition metal compound are allowed to react for at least fifteen minutes before being contacted with the olefin.

2. The process of claim 1 wherein M is titanium, zirconium or hafnium.

3. The process of claim 1 wherein T is a hydrocarboxy group, a boronate group or an amide group, preferably an alkoxide, phenoxide, acetylacetonate, or carboxylate or a cyclopentadienide group such as cyclopentadienyls, fluorenyls and indenyls.

4. The process of claim 1 wherein each Q is independently selected from the group consisting of halogens, hydrogen, alkyl, aryl, alkenyl, alkylaryl, arylalkyl, hydrocarboxy or phenoxy radicals having 1–20 carbon atoms, amides, phosphides, sulfides, silylalkyls, diketonates, and carboxylates.

5. The process of claim 1 wherein X and Y are independently nitrogen, oxygen, sulfur or phosphorus.

6. The process of claim 1 wherein Z is an aryl group.

7. The process of claim 1 wherein J is pyridine.

8. The process of claim 1 wherein the transition metal compounds is [[1-(2-Pyridyl)N-1-Methylethyl]-[1-N-2,6-Diisopropylphenyl Amido]][2-Methyl-1-Phenyl-2-Propoxy] Zirconium Dibenzyl.

9. The process of claim 1 wherein the activator is an alumoxane.

10. The process of claim 1 wherein the activator is a non-coordinating anion.

11. The process of claim 8 wherein the activator is an alumoxane.

12. The process of claim 8 wherein the activator is a modified methyl alumoxane.

13. The process of claim 1 wherein the product of the combination of the activator and the transition metal compound is combined with a metal stearate.

14. The process of claim 13 wherein the metal stearate is aluminum distearate.

15. The process of claim 1 wherein X and Y are nitrogen.

16. The process of claim 1 wherein the olefin is a monomer having 2 to 30 carbon atoms.

17. The process of claim 1 wherein the olefin comprises ethylene.

18. The process of claim 1 wherein the olefin comprises ethylene and one or more of propylene, butene-1, pentene-1,4-methyl-pentene-1, hexene-1, octene-1, decene-1, and 3-methyl-pentene-1.

19. The process of claim 1 wherein the process takes place in the gas phase.

20. The process of claim 19 wherein the catalyst composition is fed into the reactor as a solution.

21. The process of claim 19 wherein the activator is an alumoxane.

22. The process of claim 19 wherein the catalyst composition further comprises a metal stearate.

23. The process of claim 1 wherein the process occurs in the slurry phase.

24. The process of claim 23 wherein the catalyst composition is fed into the reactor as a solution.

25. The process of claim 23 wherein the activator is an alumoxane.

26. The process of claim 23 wherein the catalyst composition further comprises a metal stearate.

27. The process of claim 1 wherein the transition metal compound is contacted with solvent prior to contact with the activator.

28. The process of claim 1 further comprising a method to alter molecular weight distribution (Mw/Mn), flow index, and/or density comprising altering on line in a gas phase reactor having a volume of 1500 cubic feet or more the reaction temp and/or the hydrogen concentration and/or the activator to transition metal ratio.

* * * * *